(12) United States Patent
Wheeler et al.

(10) Patent No.: US 8,053,239 B2
(45) Date of Patent: Nov. 8, 2011

(54) DIGITAL MICROFLUIDIC METHOD FOR PROTEIN EXTRACTION BY PRECIPITATION FROM HETEROGENEOUS MIXTURES

(75) Inventors: Aaron R. Wheeler, Toronto (CA); Mais J. Jebrail, Richmond Hill (CA)

(73) Assignee: The Governing Council of the University of Toronto, Toronto, Ontario (CA)

( * ) Notice: Subject to any disclaimer, the term of this patent is extended or adjusted under 35 U.S.C. 154(b) by 541 days.

(21) Appl. No.: 12/285,567

(22) Filed: Oct. 8, 2008

(65) Prior Publication Data

US 2010/0087633 A1    Apr. 8, 2010

(51) Int. Cl.
*G01N 31/20* (2006.01)
*G01N 33/86* (2006.01)
*B01D 11/00* (2006.01)

(52) U.S. Cl. .......... 436/15; 204/451; 210/638; 210/639; 422/82.05; 422/504; 435/7.1; 435/287.3; 435/288.7; 436/86; 436/164; 436/172; 436/178; 436/180

(58) Field of Classification Search ................ 210/511, 210/634, 638, 639, 748.01, 806; 422/82.05, 422/82.08, 82.09, 100–102, 502, 504, 506, 422/627, 533; 435/6, 7.1, 287.01, 287.03, 435/287.1, 287.2, 288.6, 2, 287.3, 288.7; 436/15, 43, 63, 86, 149, 164, 169, 174, 178, 436/180, 172; 204/450, 451, 600, 601; 530/418; 366/340, 341

See application file for complete search history.

(56) References Cited

U.S. PATENT DOCUMENTS

| | | |
|---|---|---|
| 4,569,575 A | 2/1986 | Le Pesant et al. |
| 4,636,785 A | 1/1987 | Le Pesant |
| 4,818,052 A | 4/1989 | Le Pesant et al. |
| 5,486,337 A | 1/1996 | Ohkawa et al. |
| 6,007,690 A * | 12/1999 | Nelson et al. ................. 204/601 |
| 6,352,838 B1 | 3/2002 | Krulevitch et al. |
| 6,565,727 B1 | 5/2003 | Shenderov |
| 6,773,566 B2 | 8/2004 | Shenderov |
| 6,911,132 B2 | 6/2005 | Pamula et al. |
| 6,989,234 B2 | 1/2006 | Kolar et al. |
| 7,147,763 B2 | 12/2006 | Elrod et al. |

(Continued)

FOREIGN PATENT DOCUMENTS

WO    2007120241 A2    10/2007

(Continued)

OTHER PUBLICATIONS

Moon et al, "An Integrated digital microfluidic chip for multiplexed proteomic sample preparation and analysis by MALDI-MS", Jul. 2006, Lab Chip, 2006, vol. 6, pp. 1213-1219.*

(Continued)

*Primary Examiner* — Joseph Drodge
(74) *Attorney, Agent, or Firm* — Lynn C. Schumacher; Hill & Schumacher (57) ABSTRACT

A method for extracting proteins from heterogeneous fluids by precipitation using microfluidics. The method uses an automated protocol for precipitation of proteins onto surfaces, rinsing the precipitates to remove impurities, and resolubilization in buffer for further analysis. The method is compatible with proteins representing a range of different physicochemical properties, as well as with complex mixtures such as fetal bovine serum and cell lysate. In all cases, the quantitative performance (measured using a fluorescent assay for % recovery) was comparable to that of conventional techniques, which are manual and require more time.

17 Claims, 4 Drawing Sheets

U.S. PATENT DOCUMENTS

| | | | |
|---|---|---|---|
| 7,163,612 | B2 | 1/2007 | Sterling et al. |
| 7,214,302 | B1 | 5/2007 | Reihs et al. |
| 7,255,780 | B2 | 8/2007 | Shenderov |
| 7,328,979 | B2 | 2/2008 | Decre et al. |
| 7,329,545 | B2 | 2/2008 | Pamula et al. |
| 7,347,617 | B2 * | 3/2008 | Pugia et al. ............ 366/341 |
| 2001/0049148 | A1 * | 12/2001 | Wolk et al. ............ 436/180 |
| 2003/0049857 | A1 * | 3/2003 | Chan ............ 436/170 |
| 2004/0171169 | A1 | 9/2004 | Kallury et al. |
| 2004/0211659 | A1 | 10/2004 | Velev |
| 2005/0115836 | A1 | 6/2005 | Reihs |
| 2005/0148091 | A1 | 7/2005 | Kitaguchi et al. |
| 2005/0191759 | A1 | 9/2005 | Pedersen-Bjergaard et al. |
| 2006/0003439 | A1 * | 1/2006 | Ismagilov et al. ......... 435/287.2 |
| 2007/0023292 | A1 | 2/2007 | Kim et al. |
| 2007/0148763 | A1 | 6/2007 | Huh et al. |
| 2007/0242111 | A1 | 10/2007 | Pamula et al. |
| 2008/0044914 | A1 | 2/2008 | Pamula et al. |
| 2008/0156983 | A1 | 7/2008 | Fourrier et al. |
| 2008/0185339 | A1 | 8/2008 | Delapierre et al. |
| 2009/0014394 | A1 * | 1/2009 | Yi et al. ............ 210/767 |
| 2009/0203063 | A1 | 8/2009 | Wheeler et al. |
| 2010/0015614 | A1 * | 1/2010 | Beer et al. ............ 435/6 |
| 2010/0081578 | A1 | 4/2010 | Wheeler et al. |
| 2010/0087633 | A1 | 4/2010 | Wheeler et al. |
| 2010/0311599 | A1 | 12/2010 | Wheeler et al. |

FOREIGN PATENT DOCUMENTS

| | | |
|---|---|---|
| WO | 2007136386 A3 | 11/2007 |
| WO | 2008051310 A3 | 5/2008 |

OTHER PUBLICATIONS

Chaterjee et al, "Droplet-based microfluidics with nonaqueous solvents and solutions", Jan. 2006, Lab Chip, 2006, vol. 6, pp. 199-206.*

Teh et al, "Droplet microfluidics", Jan. 2008, Lab on a Chip, 2008, vol. 8, pp. 198-220.*

Lee et al., "Removal of bovine serum albumin using solid-phase extraction with in-situ polymerized stationary phase in a microfluidic device", Journal of Chromatography A, 2008, vol. 1187, pp. 11-17, Elsevier.

Tan et al., A lab-on-a-chip for detection of nerve agent sarin in blood, Lab Chip, 2008, vol. 8, pp. 885-891.

Kai-Cheng Chuang. "Direct Handwriting Manipulation of Droplets by Self-Aligned Mirror-EWOD Across a Dielectric Sheet," MEMS (Jan. 2006) pp. 22-26.

Mohamed Abdelgawad. "Low-cost, rapid-prototyping of digital microfluidic devices," Springer, Microfluid Nanofluid (2008) vol. 4, pp. 349-356.

Eric Lebrasseur. "Two-dimensional electrostatic actuation of droplets using a single electrode panel and development of disposable plastic film card," ScienceDirect, Sensors and Actuators (2007) vol. 136, pp. 358-386.

Mais J. Jebrail. "Digital Microfluidic Method for Protein Extraction by Precipitation," Anal. Chem. (2009) vol. 81, No. 1.

Hyejin Moon. An integrated digital microfluidic chip for multiplexed proteomic sample preparation and analysis by MALDI-MS, The Royal Society of Chemistry (2006), Lab Chip vol. 6, pp. 1213-1219.

Debalina Chatterjee. "Droplet-based microfluidics with nonaqueous solvents and solutions," The Royal Society of Chemistry (2006), Lab Chip vol. 6, pp. 199-206.

Darren R. Link. "Electric Control of Droplets in Microfluiclic Devices." Communications, Angew Chem. Int (2006) vol. 45 pp. 2556-2560.

A.S. Verkman, "Drug Discovery in Academia," Am J Physiol Cell Physiol (2004) vol. 286, pp. 465-474.

Marc A. Unger. "Monolithic Microfabricated Valves and Pumps by Multilayer Soft Lithography," Science (2000) vol. 288.

Jamil El-Ali. "Cells on chips," Nature (2006) Insight Review, vol. 442.

Shih-Kang Fan. "Cross-scale electric manipulations of cells and droplets by frequency-modulated dielectrophoresis and electrowetting" The Royal Society of Chemistry (2008), Lab Chip vol. 8, pp. 1325-1331.

Ting-Hsuan Chen. "Selective Wettability Assisted Nanoliter Sample Generation Via Electrowetting-Based Transportation," Proceedings of the Fifth International Conference on Nanochannels, Microchannels and Minichannels (ICNMM) (Jun. 18-20, 2007).

Hongmei Yu. "A plate reader-compatible microchannel array fear cell biology assays," The Royal Society Chemistry (2007) Lab Chip vol. 7, pp. 388-391.

Wheeler Aaron A. "Electrowetting-Based Microfluidics for Analysis of Peptides and Proteins by Matrix-Assisted Laser Desorption/Ionization Mass Spectrometry," (Aug. 2004) Anal Chem. vol. 76, No. 16.

* cited by examiner

DIGITAL MICROFLUIDIC METHOD FOR PROTEIN EXTRACTION BY PRECIPITATION FROM HETEROGENEOUS MIXTURES

FIELD OF THE INVENTION

The present invention relates to a method for protein extraction by precipitation from heterogeneous mixtures using digital microfluidics.

BACKGROUND OF THE INVENTION

In the post-genome era, proteomics has emerged as the next great scientific challenge. While methodologies vary widely, a near-universal first step for proteomic analyses of physiological samples (e.g., blood, serum, tissue extract, etc.) is removal of the non-relevant solution constituents (e.g., nucleic acids, lipids, etc.).[1-4] A common method used to accomplish this task is protein precipitation. In this technique, one or more precipitants (organic solvents, salts, or pH modulators) is mixed with the protein-containing sample, which causes proteins to precipitate and settle to the bottom of the reaction vessel.[1-3,5-8] After centrifuging, removal of supernatant, and washing in appropriate rinse solvents, the precipitate can be re-dissolved, and the now-purified solution can be used for subsequent processing and analysis.

The present invention discloses the development of an automated, microfluidic method for extracting proteins from heterogeneous fluids by precipitation. Although there have been myriad applications of microfluidic technologies to proteomics,[9] to the inventor's knowledge, there have been no disclosures describing protein extraction by precipitation in microchannels. It is noted that precipitation has been used in channels to remove proteins for analysis of other analytes,[10] but not as a technique to extract and collect proteins for further analysis. The inventors speculate that this deficit is a function of complexity and heterogeneity since in protein extraction by precipitation, liquids (samples, rinse solutions, etc.), solids (precipitates), and vapor phases (air for drying precipitates) all play a prominent roles and must be precisely controlled. These requirements seem like a poor match for the conventional format for microfluidics, enclosed microchannels. Thus, in the current work, we chose to use the alternative format of digital microfluidics (DMF).

In DMF, discrete droplets of sample and reagents are controlled (i.e., moved, merged, mixed, and dispensed from reservoirs) by applying a series of electrical potentials to an array of electrodes.[11,12] Because of its reconfigurability and scalability, DMF has recently become popular for a wide range of biochemical applications including cell-based assays,[13] enzyme assays,[14-16] protein profiling,[17-19] and the polymerase chain reaction.[20] More importantly, the DMF format seems well suited for complex procedures such as protein extraction by precipitation, as DMF can be used to precisely control liquid-, solid-, and gas-phase reagents in heterogeneous systems.[21-24]

It would therefore be very advantageous to provide an automated method for extracting and purifying proteins from heterogeneous mixtures using digital microfluidics as this would facilitate high throughput extraction and screening of proteins.

SUMMARY OF INVENTION

The present invention provides embodiments of devices and methods for automated, DMF-based protocol for extracting and purifying proteins from heterogeneous mixtures, including the key steps of precipitation, rinsing, and resolubilization. The effectiveness of the new method was determined using electrospray ionization mass spectrometry (ESI-MS), and the % recovery was quantified using fluorescence. The method is demonstrated to be compatible with protein standards representing a range of different physicochemical properties, as well as with complex mixtures such as fetal bovine serum and cell lysate. In all cases, the performance of the new method was comparable to that of conventional techniques, with the advantages of automation and reduced analysis time. This present invention very advantageously facilitates the development of fully automated microfluidic methods for proteomic analyses.

Thus, the present invention provides a digital microfluidic based method for protein extraction by precipitation from heterogeneous mixtures, comprising the steps of:

a) providing a digital microfluidic device having an array of actuating electrodes formed on a substrate surface, a coating having a hydrophobic working surface coating the substrate surface and array of actuating electrodes, an actuating electrode controller for exciting or de-exciting said actuating electrodes for translating liquid droplets over said hydrophobic working surface;

b) dispensing one or more first sample droplets containing protein, onto one or more first positions on the hydrophobic working surface, and dispensing one or more second droplets containing a protein precipitant onto one or more second positions on the hydrophobic working surface;

c) translating each of the one or more first and second droplets to one or more corresponding designated protein extraction positions on the hydrophobic working surface such that they substantially mix to form one or more secondary droplets;

d) incubating the one or more secondary droplets at the designated one or more corresponding extraction positions to precipitate the protein contained in the one or more first droplets onto the one or more designated protein extraction positions to separate the precipitated protein from a drop of supernatant above the precipitate;

e) actuating one or more of said discrete electrodes associated with the one or more corresponding extraction positions to remove the one or more droplets of supernatant from the one or more corresponding extraction positions to leave behind the precipitated protein;

f) dispensing one or more third droplets containing wash solution onto said hydrophobic working surface and translating said one or more third droplets to said one or more corresponding extraction positions to wash the precipitated protein;

g) drying the precipitated protein at the one or more extraction positions;

h) dispensing one or more fourth droplets containing resolubilization solution onto said hydrophobic working surface and translating said one or more fourth droplets to said one or more corresponding extraction positions to produce one or more droplets of resolubilized protein; and i) translating the one or more droplets of resolubilized protein to one or more collection points on said hydrophobic working surface and collecting the one or more droplets of resolubilized protein.

In another embodiment of the present invention there is provided a digital microfluidic based method for protein extraction by precipitation from heterogeneous mixtures, comprising the steps of:

a) providing a digital microfluidic device having an array of actuating electrodes formed on a substrate surface, a coating having a hydrophobic working surface coating the substrate surface and array of actuating electrodes, an actuating electrode controller for exciting or de-exciting said actuating electrodes for translating liquid droplets over said hydrophobic working surface;

b) depositing a protein precipitant on one or more designated protein extraction positions on the working surface;

c) dispensing one or more first sample droplets containing protein onto one or more first positions on the hydrophobic working surface;

d) translating each of the one or more first droplets to one or more of the corresponding designated protein extraction positions on the working surface such that they substantially mix with the protein precipitant to form one or more secondary droplets;

e) incubating the one or more secondary droplets at the designated one or more corresponding extraction positions to precipitate the protein contained in the one or more first droplets onto the one or more designated protein extraction positions to separate the precipitated protein from a drop of supernatant above the precipitate;

f) actuating one or more of said discrete electrodes associated with the one or more corresponding extraction positions to remove the one or more droplets of supernatant from the one or more corresponding extraction positions to leave behind the precipitated protein;

g) dispensing one or more third droplets containing wash solution onto said working surface and translating said one or more third droplets to said one or more corresponding extraction positions to wash the precipitated protein;

h) drying the precipitated protein at the one or more extraction positions;

i) dispensing one or more fourth droplets containing resolubilization solution onto said hydrophobic working surface and translating said one or more fourth droplets to said one or more corresponding extraction positions to produce one or more droplets of resolubilized protein; and j) translating the one or more droplets of resolubilized protein to one or more collection points on said hydrophobic working surface and collecting the one or more droplets of resolubilized protein.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

Without limitation, the majority of the systems described herein are directed to protein extraction by precipitation from heterogeneous mixtures using digital microfluidics. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to protein extraction by precipitation from heterogeneous mixtures using digital microfluidics.

As used herein, the term "about" and the symbol "~", when used in conjunction with ranges of dimensions, temperatures or other physical and/or chemical properties and/or characteristics is meant to cover slight variations that may exist in the upper and lower limits of the ranges of dimensions as to not exclude embodiments where on average most of the dimensions are satisfied but where statistically dimensions may exist outside this region. For example, in embodiments of the present invention dimensions of a digital microfluidic device are given but it will be understood that these are not meant to be limiting.

In the invention disclosed herein, an automated, DMF-based protocol is provided for extracting and purifying proteins from heterogeneous mixtures, including the key steps of precipitation, rinsing, and resolubilization. The effectiveness of the new method was determined using electrospray ionization mass spectrometry (ESI-MS), and the % recovery was quantified using fluorescence. The method was demonstrated to be compatible with protein standards representing a range of different physicochemical properties, as well as with complex mixtures such as fetal bovine serum and cell lysate. In all cases, the performance of the new method was comparable to that of conventional techniques, with the advantages of automation and reduced analysis time. This work is an important first step in our efforts to develop fully automated microfluidic methods for proteomic analyses.

The present invention will now be illustrated with the following non-limiting examples of protein extraction by precipitation from heterogeneous mixtures using digital microfluidics, and those skilled in the art will appreciate that these are meant to be exemplary only, and not limiting in any way.

Reagents and Materials

Acetone, acetonitrile (ACN), chloroform, methanol, boric acid, 50% formic acid, fluorinert FC-40, sodium hydroxide, Pluronic F127, trichloroacetic acid (TCA), Triton X-100, phenylmethylsulfonyl fluoride (PMSF), sodium dodecyl sulfate (SDS), fluorescamine, ammonium sulfate, bovine serum albumin (BSA), fibrinogen (Fb), and myoglobin (Mb) were purchased from Sigma Chemical (Oakville, ON). Dulbecco's phosphate buffered saline (PBS) and fetal bovine serum (FBS) were purchased from Invitrogen Canada (Burlington, Ontario). 1,2-Dibutyroyl-sn-glycero-3-phosphocholine (PC) was purchased from Avanti Polar Lipids Inc. (Alabaster, Ala.). In all experiments, solvents of HPLC-grade and deionized (DI) water with a resistivity of 18 MΩ·cm at 25° C. were used.

Working solutions of all proteins were prepared in 10 mM borate buffer (pH 8.5) with 0.08% Pluronics F127 (w/v).[25] For qualitative analysis of protein extraction, a test solution containing 0.71 mM protein (Mb) and 62 mM lipid (PC) was prepared. For quantitative analysis of protein recovery, solutions of BSA (50 mg/mL), Mb (30 mg/mL), and Fb (20 mg/mL) were prepared. For experiments involving FBS and cell lysate, solutions included 0.08% Pluronics F127. Protein precipitation methods used trichloroacetic acid (TCA) (20% in DI water), acetonitrile (ACN), and ammonium sulfate (saturated solution in DI water) as the precipitants and acetone, chloroform/ACN (70/30 v/v), and chloroform/acetone (60/40 v/v) as rinse solutions.

Clean-room reagents and supplies included Shipley S1811 photoresist and MF321 developer from Rohm and Haas (Marlborough, Mass.), AZ300T photoresist stripper from AZ Electronic Materials (Somerville, N.J.), parylene C dimer from Specialty Coating Systems (Indianapolis, Ind.), Teflon-AF from DuPont (Wilmington, Del.), solid chromium and gold from Kurt J. Lesker Canada (Toronto, ON), CR-4 chromium etchant from Cyantek (Fremont, Calif.), hexamethyldisilazane (HMDS) from Shin-Etsu MicroSi (Phoenix, Ariz.), and concentrated sulfuric acid and hydrogen peroxide (30%) from Fisher Scientific Canada (Ottawa, ON). Piranha solution was prepared as a 3/1 v/v mixture of sulfuric acid/hydrogen peroxide.

Cell Culture and Analysis

Jurkat T-cells were maintained in a humidified atmosphere (5% $CO_2$, 37° C.) in RPMI 1640 medium supplemented with 10% fetal bovine serum, penicillin (100 IU $mL^{-1}$), and streptomycin (100 μg $mL^{-1}$). Cells were subcultured every 3-4 days at $5 \times 10^5$ cells $mL^{-1}$. Lysing medium was PBS with 0.08% (wt/v) F 127, 1% Triton X-100, and 1 mM PMSF. For precipitation experiments, cells were washed once in PBS, suspended in lysing medium at $6 \times 10^7$ cells $mL^{-1}$, incubated on ice (30 min), and centrifuged (13 000 rpm, 5 min). The supernatant was collected and stored at −80° C. until use.

Device Fabrication and Operation

Digital microfluidic devices were fabricated using conventional methods in the University of Toronto Emerging Communications Technology Institute (ECTI) cleanroom facility, using a transparent photomask printed at Norwood Graphics (Toronto, ON). Glass wafers (Howard Glass Co. Inc., Worcester, Mass.) were cleaned in piranha solution (10 min), and then coated with chromium (250 nm) by electron beam deposition. After rinsing and drying, the substrates were primed by spin-coating with HMDS (3000 rpm, 30 s) and then spin-coated again with Shipley S1811 photoresist (3000 rpm, 30 s). Substrates were pre-baked on a hotplate (100° C., 2 min), and then exposed to UV radiation (35.5 mW $cm^{-2}$, 365 nm, 4 s) through a photomask using a Karl Suss MA6 mask aligner (Garching, Germany).

After exposure, substrates were developed in MF-321 (3 min), and then post-baked on a hot plate (100° C., 1 min). Following photolithography, substrates were immersed in chromium etchant (30 s). The remaining photoresist was stripped in AZ-300T (10 min). After forming electrodes and cleaning in piranha solution (30 s), substrates were coated with 2.5 μm of Parylene-C and 50 nm of Teflon-AF. Parylene-C was applied using a vapor deposition instrument (Specialty Coating Systems), and Teflon-AF was spin-coated (1% wt/wt in Fluorinert FC-40, 2000 rpm, 60 s) followed by post-baking on a hot-plate (160° C., 10 min). The polymer coatings were removed from contact pads by gentle scraping with a scalpel to facilitate electrical contact for droplet actuation. In addition to patterned devices, unpatterned indium tin oxide (ITO) coated glass substrates (Delta Technologies Ltd, Stillwater, Minn.) were coated with Teflon-AF (50 nm, as above).

Figure 1A:
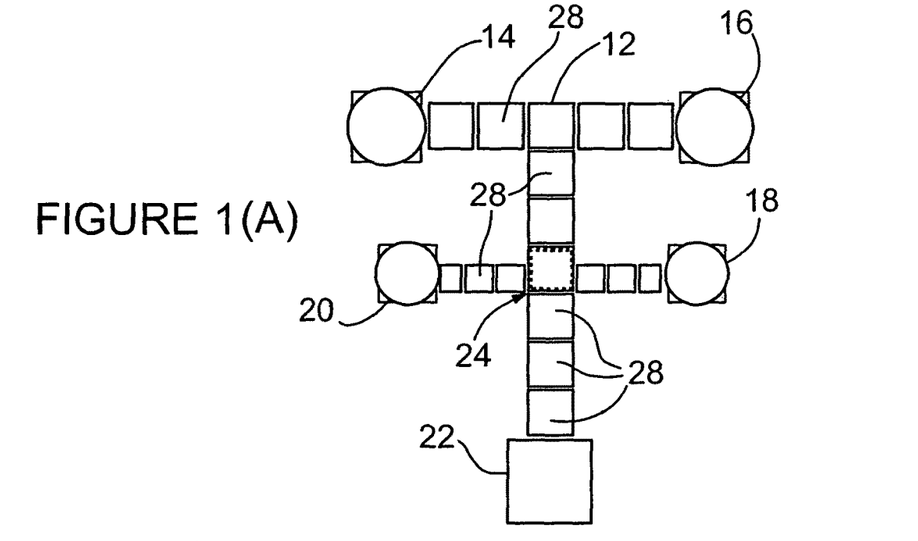
FIG. 1(a) shows top plan view of a digital microfluidic device showing four reagent reservoirs, a waste reservoir, and extraction electrode.

The devices had a double-cross geometry as shown in FIG. 1(a) to be described in more detail hereinafter, with 1×1 and 1.5×1.5 mm actuation electrodes, 2.5×2.5 mm and 3.0×3.0 mm reservoir electrodes, and inter-electrode gaps of 40 μm. Devices were assembled with an unpatterned ITO-glass top plate and a patterned bottom plate separated by a spacer formed from one or two pieces of double-sided tape (70 or 140 μm thick). Driving potentials (70-100 $V_{RMS}$) were generated by amplifying the output of a function generator (Agilent Technologies, Santa Clara, Calif.) operating at 18 kHz. As described elsewhere,[13] droplets were sandwiched between the two plates and actuated by applying driving potentials between the top electrode (ground) and sequential electrodes on the bottom plate via the exposed contact pads. Droplet actuation was monitored and recorded by a CCD camera mounted on a lens.

DMF-Driven Protein Extraction

Protocols were developed using digital microfluidics to implement protein extraction by precipitation and resolubilization. In each experiment, droplets containing the sample (i.e., protein standards, mixtures, FBS, or cell lysate) and a precipitant were dispensed from their respective reservoirs and merged on the extraction electrode. In some cases, a third droplet containing a secondary precipitant was also dispensed and merged. The combined droplet was allowed to incubate until the protein was observed to precipitate from solution (~5 min, room temperature), after which the supernatant was actuated away from the extraction electrode (to the waste reservoir). The precipitate was then washed by dispensing and driving three droplets of rinse solution across the extraction electrode to waste. The precipitate was dried and a droplet of resolubilization solution was dispensed and driven to the extraction electrode to dissolve the protein. In some cases the precipitate was baked on a hot plate (95° C., 5 min) prior to resolubilization to ensure complete removal of any aqueous residue.

The composition of precipitant(s), rinse solutions, and resolubilization solutions were optimized for each analyte and are recorded in Table 1. For protocols applied to standards, mixtures, and serum, sample and precipitant droplet volumes were ~140 nL and rinse and resolubilization solution droplet volumes were ~315 nL. For the protocol applied to cell lysate, the corresponding volumes were ~70 and ~158 nL, respectively.

Conventional Protein Extraction

Protein samples were extracted on the macroscale by combining 10 μL of sample with 10 μL chilled precipitant in a microcentrifuge tube. The solution was incubated (5 min, 4° C.) and then centrifuged (13,000 rpm, 5 min), and the supernatant was discarded. The pellet was washed three times by iteratively suspending in rinse solution (22.5 μL) and centrifuging (13,000 rpm, 5 min) and discarding the supernatant. The final pellet was dissolved in 100 μL. The precipitant, rinse solution, and resolubilization solution for each analyte were identical to those used for DMF.

Mass Spectrometry

Extracts of PC/Mb mixtures were evaluated qualitatively by mass spectrometry. Briefly, 315-nL samples (prepared by DMF as described above) were diluted into 50 µL of 50/50 water/ACN containing 0.1% formic acid and injected into an LTQ linear ion trap mass spectrometer (Thermo Fischer Scientific, Waltham, Mass.) operating in positive ion mode. Samples were delivered via a fused silica capillary transfer line (100 µm i.d.) mated to a New Objective Inc. (Woburn, Mass.) nanoelectrospray emitter (100 µm i.d. tapering to 30 µm i.d.). The samples were delivered at a flow rate of 0.5 µL min$^{-1}$, with an applied voltage of 1.7-1.9 kV and capillary temperature of 170° C. Spectra were collected as an average of 50 acquisitions, and data shown here are representative of analysis of samples in triplicate.

Fluorescence

Extraction efficiency was evaluated quantitatively using a fluorescence-based assay. For samples prepared by DMF, 315- or 158-nL droplets (as above) of sample were diluted into 13-µL aliquots of pH 8.5 working buffer in wells in a 384-well low-volume microplate. The working buffers were identical to the resolubilizing buffers (Table 1). Upon addition of 2 µL of fluorescamine (5 mg/mL in acetone) the microplate was inserted into a fluorescence microplate reader (Pherastar, BMG Labtech, Durham, N.C.) equipped with a module for 390 nm excitation and 510 nm emission. The plate was shaken (1 min), allowed to sit (2 min), and then the fluorescence was measured.

As a control, for each analyte, identical samples that had not been extracted were evaluated using the same fluorescent assay. To ensure that controls were processed in identical volumes relative to extracted samples, each control was prepared by dispensing a droplet on a device, delivering it to the extraction electrode, and allowing it to dry. A droplet of resolubilization solution was then dispensed, driven to the dried spot, incubated to allow for full dissolution, and the droplet was collected and analyzed. Four replicate measurements were made for each sample and control.

For samples extracted using conventional methods, the quantitative analysis protocol was similar to that used for samples prepared by DMF, with identical working buffers and reagents. The difference was volume—in each case, precipitate from 10 µL samples were resolubilized in 100-µL working buffer. Each sample was mixed with 13 µL fluorescamine (5 mg/mL in acetone) in a well in a 96-well plate. As with samples prepared by DMF, controls were evaluated, and four replicate trials were conducted for each sample and control.

Device and Method Optimization

In an automated method for protein extraction by precipitation, at least four different solutions are managed including sample solution, precipitant solution, rinse solution solution, and resolubilization solution. To facilitate this goal, as shown in FIG. 1(a), a digital microfluidic device 10 with a "double T" electrode array 12 defining a pattern of discrete electrodes 28 is shown, with four reservoirs 14 (rinse solution), 16 (resolubilizing buffer), 18 (BSA solution) and 20 (precipitant solution) with dedicated droplet movement paths) for the various reagents, and a fifth reservoir 22 is for waste. The dimensions of the electrodes 12 were chosen such that (in normal circumstances) the droplet volumes were 140 nL (sample and precipitant) and 315 nL (rinse and resolubilization solutions), respectively.

The device can have more than one dielectric layer (not shown) on top of the electrode array and substrate on which the array 12 is located. Located on top of the dielectric material is a hydrophobic layer (not shown) for example Teflon AF, 50 nm. The array of actuating electrodes 12 and exposed areas of substrate surface are thus covered by a working surface. In an embodiment of the device, spaced above electrodes array 12/dielectric layer. Counter or reference electrodes form part of the device as part of the electrical circuit for actuating the discrete electrodes. A two plate device may also be used (not shown). For example, as mentioned above DFM devices were assembled with an unpatterned ITO-glass top plate and a patterned bottom plate (on which the electrode array 12 is patterned, with a hydrophobic working surface separated by a spacer formed from one or two pieces of double-sided tape (70 or 140 µm thick).

Further details of various embodiments of DMF devices that may be constructed are disclosed in copending U.S. patent application Ser. No. 12/285,020, entitled "DROPLET-BASED CELL CULTURE AND CELL ASSAYS USING DIGITAL MICROFLUIDICS", filed on Sep. 26, 2008, which is incorporated herein in its entirety by reference.

As shown, a key position in the design is the extraction electrode 24, the hydrophobic surface above this electrode is where the precipitation and purification of proteins takes place. In practice, samples were sequentially precipitated onto the extraction electrode 24, washed in rinse solution, and then resolubilized in solvent. It is noted while extraction electrodes 24 form one or more corresponding designated protein extraction positions on the hydrophobic working surface, these sites do not have to sit directly above a discrete electrode 28 but could be over a gap between neighboring discrete electrodes as long as these sites are readily accessible to droplets being translated across the surface by electrode array 12.

Protein precipitation may be performed with multiple droplets simultaneously or sequentially in a certain order defined by a selected protocol. For example, a computer controller interfaced to the device reservoirs and associated dispensing devices is programmed to dispense droplets of the sample and droplets of one or more cell reagents onto the top working surface of the dielectric layer covering the electrode array, and translating them over the array of actuating electrodes for mixing the droplets in selected positions on the array of actuating electrodes to form one or more secondary droplets in a selected order defined by a selected protocol for which the computer controller is programmed.

Moreover, precipitation on DMF platform can also be initiated by having the precipitant (in the solid form) pre-deposited on the extraction electrode and when precipitation of proteins is required the sample droplets can be brought to the pre-deposited extraction electrode and begin precipitation. For example, the protein precipitant in solid form may be ammonium sulfate and trichloroacetic acid. In this case the solid precipitant may be laid down at the designated precipitation locations to form an array and the droplets of sample brought to these sites.

The sample droplets containing protein may include, but is not limited to, any one or combination of protein standards, mixtures, bovine serum albumin, myoglobin, insulin, fibrinogen, fibronectin, fetal bovine serum, cell lysate, tissue powder, plasma, whole blood.

Typical precipitant solutions include, but is not limited to, any one or combination of trichloroacetic acid (TCA), acetonitrile, acetone, ethanol, mercaptoethanol, chloroform, and polyethylene glycol, dextran, and ammonium sulfate.

The resolubilization solution includes, but is not limited to, any one or combination of borate, sodium hydroxide, potassium carbonate, tris(hydroxymethyl)aminomethane hydrochloride (Tris-HCl), urea, thiourea, trizma base, triton X-100, 3-[(cholamidopropyl)dimethylamino]-1-propanesulfonate (CHAPS), dithiothreitol (DTT), and sodium dodecyl sulfate (SDS), LKP ampholines.

Figure 1B:
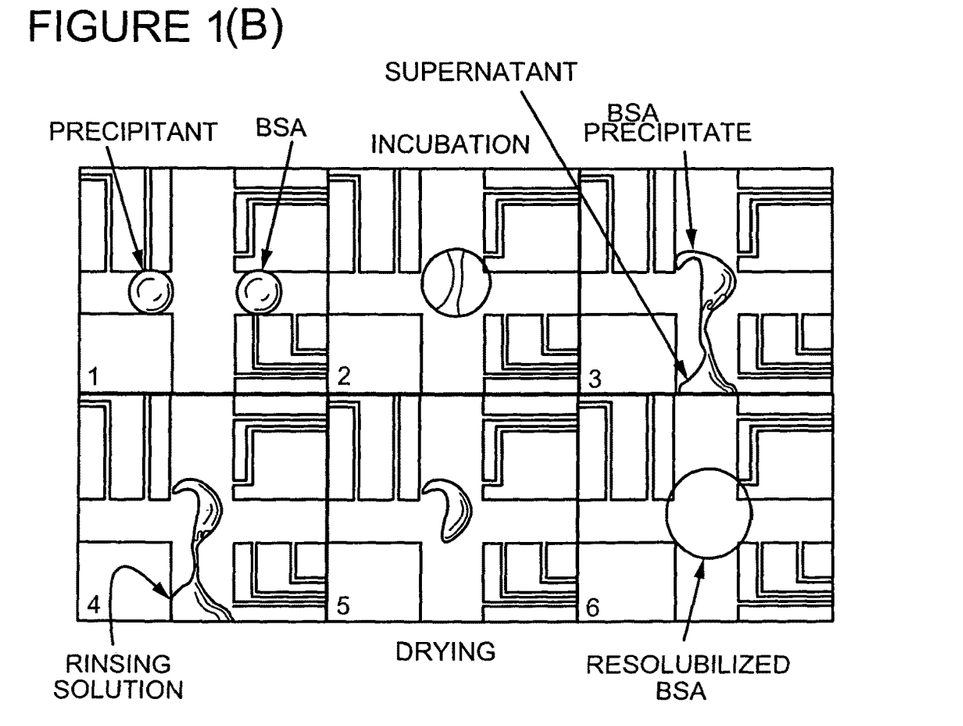
FIG. 1(b) shows frames from a movie depicting the extraction and purification of BSA (50 mg/mL) in 20% TCA (precipitant) and washing with 70/30 v/v chloroform/acetonitrile (rinse solution) using the device of FIG. 1(a), in the final frame, the precipitated protein is redissolved in a droplet of 100 mM borate buffer containing 1% SDS.

FIG. 1(b) shows frames 1 to 6 from a movie depicting the extraction and purification of BSA (50 mg/mL) in 20% TCA (precipitant) and washing with 70/30 v/v chloroform/acetonitrile (rinse solution) using the device of FIG. 1(a). As shown, a droplet containing BSA is merged with a droplet containing 20% TCA to precipitate the protein in frame 2 followed by incubation. After precipitation, the supernatant was driven away to the waste reservoir leaving the precipitate on the extraction electrode, frame 3. The precipitate was then washed in three droplets of 70/30 chloroform/ACN and allowed to dry, frames 4 and 5. Finally, in the final frame 6 the purified protein was resolubilized in a droplet of 100 mM borate (pH 8.5) buffer containing 1% SDS.

As is the case for conventional methods,[7] the inventors have found that the optimal DMF-driven recipe for protein precipitation varies from sample to sample (Table 1). For example, ACN worked well as a precipitant for highly concentrated solutions of Mb and Fb. Low concentrations (<1 mM) were more challenging, for example, reproducible precipitation and extraction of 0.71 mM myoglobin required two different precipitants, including concentrated ammonium sulfate. For samples containing proteins and phospholipids, chloroform was found to be a useful rinsing agent to remove residues of the phospholipid from the precipitate. However, because neat chloroform is not amenable to actuation at low driving potentials (as reported previously[26]), a mixture of chloroform and ACN (70/30 v/v) (which was readily movable) was used. As has been reported,[1,2,6] TCA was the best precipitant for large proteins and complex mixtures (BSA, FBS, and cell lysate). For BSA and FBS, acetone was found to be a useful rinsing agent to remove traces of TCA from the precipitate. For cell lysate, however, neat acetone was found to dissolve some of the precipitated protein; thus, a mixture of chloroform and acetone (60/40 v/v) was used. In all experiments, borate buffer containing SDS worked well for resolubilization, although in future work, we may experiment with alternatives (e.g., acid labile surfactants, urea, etc.).

TABLE 1

Solutions used for extracting, purifying, and resolubilizing proteins.

| Sample | Primary Precipitant | Secondary Precipitant | Rinse Solution | Resolubilizing Solution |
|---|---|---|---|---|
| Mb | ACN | — | Chloroform/ACN (70/30 v/v) | 10 mM Borate with 1% SDS |
| Fb | " | — | Chloroform/ACN (70/30 v/v) | 10 mM Borate with 1% SDS |
| Mb/PC | " | Ammonium Sulfate (saturated in DI) | Chloroform/ACN (70/30 v/v) | 10 mM Borate with 1% SDS |
| BSA | 20% TCA | — | Chloroform/ACN (70/30 v/v) | 100 mM Borate with 1% SDS |
| FBS | " | — | Acetone | 100 mM Borate with 10% SDS |
| Cell Lysate | " | — | Chloroform/Acetone (60/40 v/v) | 100 mM Borate with 10% SDS |

The protein extraction method reported here differs from conventional techniques in many respects, but one difference stands out: no centrifugation is required. In initial experiments, we observed that precipitates in droplets settle much more quickly than they do in centrifuge tubes. This is largely a function of distance, the maximum path in DMF samples is ~0.1 μm, while the comparable parameter in microcentrifuge tubes or well plates is several millimetres. Moreover, once settled, precipitates in DMF devices adhere strongly to the Teflon-AF device surfaces. This is fortuitous, as it facilitates the process of separating the liquid phase from solid (FIG. 1(b) frames 3-4). These characteristics make the DMF-based extraction procedure faster by a factor of two relative to the macroscale equivalent (from ~30 to ~15 min).

Evaluation of Method Efficiency

Figure 2:
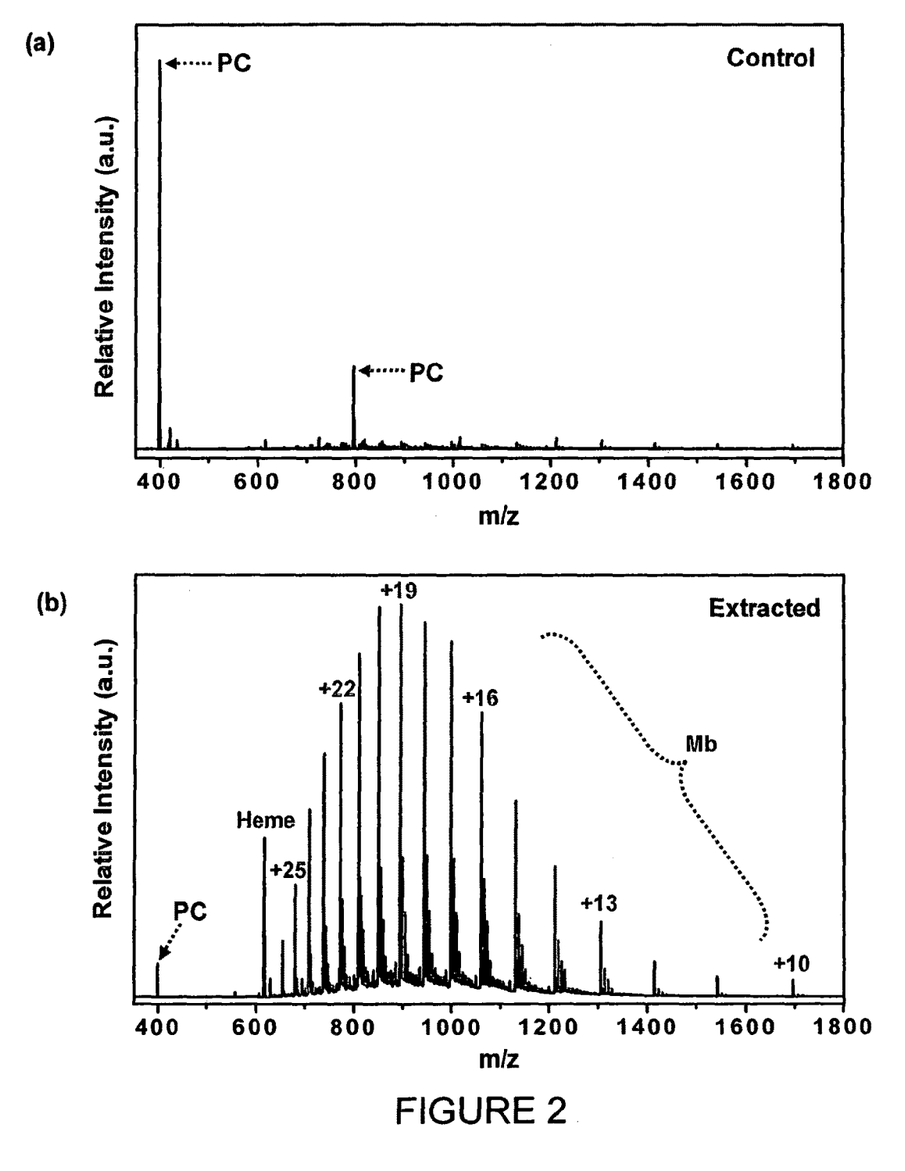
FIG. 2(a) shows ESI-MS spectra of a control.
FIG. 2(b) shows ESI-MS spectra of extracted samples containing model analyte, Mb (0.71 mM) and model contaminant, PC (62 mM)

To qualitatively evaluate the effectiveness of on-chip protein extraction, a model system comprising a protein analyte (Mb) and a phospholipid contaminant (PC) was used. To evaluate a "worst case" scenario, the concentrations were chosen to have a large excess (80:1) of contaminant. FIGS. 2(a) and (b) shows representative mass spectra generated from control and extracted solutions. As shown, in the spectrum of the control sample (FIG. 2(a)), there are two prominent peaks at m/z 398 and 795 representing the $[M+1]^{+1}$ and $[2M+1]^{+1}$ ions of PC. A close look at the spectrum reveals a noisy baseline in the 600-1,800 m/z region corresponding to a low signal from Mb, which is suppressed by the high concentration of contaminant. In the spectrum of the extracted sample (FIG. 2(b)), the peaks in the 600-1,800 m/z region correspond to the multiply charged ions of Mb (+27 to +10). An additional peak at m/z 616 represents the $[M+1]^{+1}$ ion of dissociated Heme cofactor. A very small peak at m/z 398 corresponds to the trace PC that remains in the solution. As shown, this method is a qualitative success, transforming a contaminated sample with very little analyte signal into a much purer solution that contains primarily analyte.

To quantitatively evaluate the extraction efficiency of the new DMF techniques, we used a fluorescence-based assay similar to the widely used absorbance-based Bradford test.[27] The fluorescent method relies on fluorescamine, a fluorogenic reagent that exhibits no fluorescence until it reacts with primary amines, such as those at the N-terminus of proteins.[28,29] The reaction is immediate, and is used for non-specific labelling and quantification of proteins in solution.[30,31] Three proteins representing a range of physicochemical characteristics, BSA (MW 66 kDa, pI 4.7), Mb (17 kDa, pI 7.3 & 6.8), and Fb (MW 340 kDa, pI 5.5) were evaluated at different concentrations to determine the range of linear response. Concentrations found to be in this range (50, 30, and 20 mg/mL of BSA, Mb, and Fb respectively) were chosen for quantitative analysis, and % recovery was determined by comparing the fluorescence intensity of multiple samples before and after extraction. For comparison, the same samples and concentrations were also extracted from 10 μL aliquots in pipette tubes.

Figure 3:
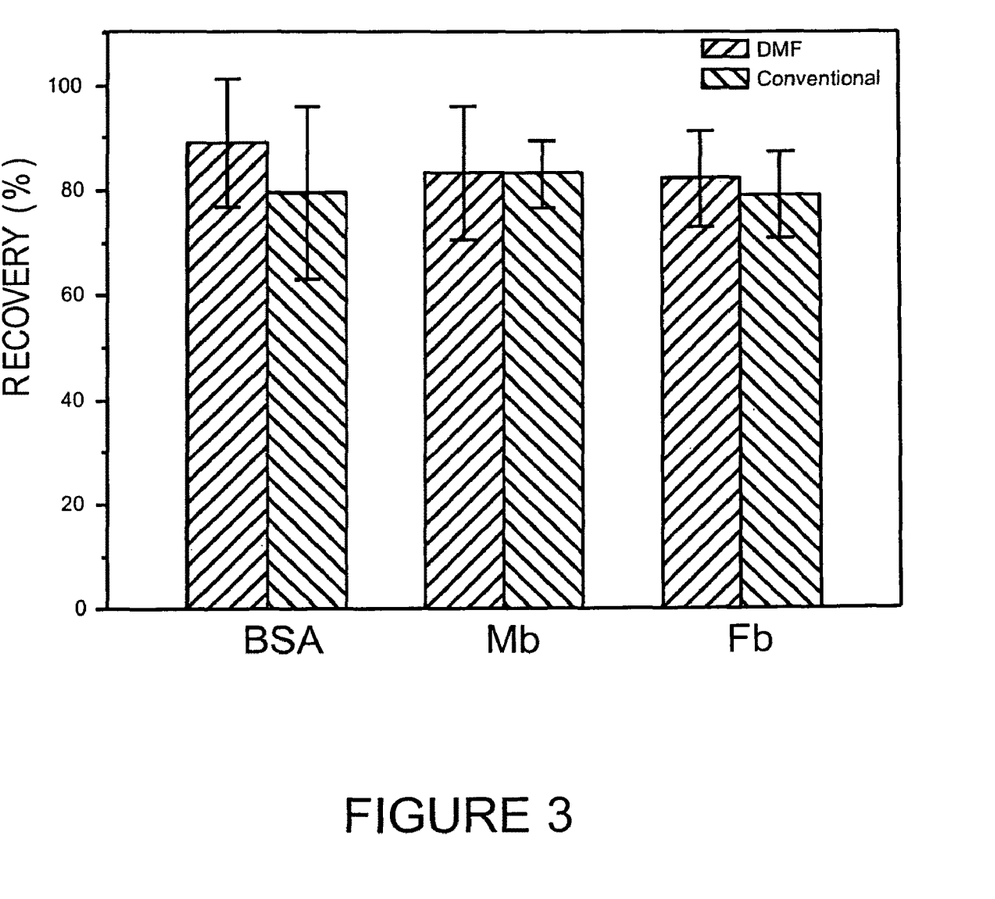
FIG. 3 is a bar graph comparing the recovery efficiency for protein standards using the DMF method (blue bars) and conventional macroscale techniques (pipette, centrifuge, etc.) (red bars), in each experiment, BSA (50 mg/mL), Mb (30 mg/mL), or Fb (20 mg/mL) samples were precipitated, washed, resolubilized, and reacted with fluorescamine, and the fluorescence intensity was compared with that of a control, the data represent the mean±S.D. of 4 extractions for each condition.

As shown in FIG. 3, the new digital microfluidic method proved to be very efficient, over 80% was recovered for each protein standard evaluated. In initial experiments, we hypothesized that macroscale methods might have better recovery, as the centrifugation step might facilitate collection of very small, non-settling precipitate particles. However, we did not observe this to be the case—as shown, the efficiencies determined for the new method were comparable or better than those calculated for standard techniques. In short, the new method seems to be a truly analogous procedure, with the advantages of automation and shorter processing times.

Application to Complex Solutions

Figure 4:
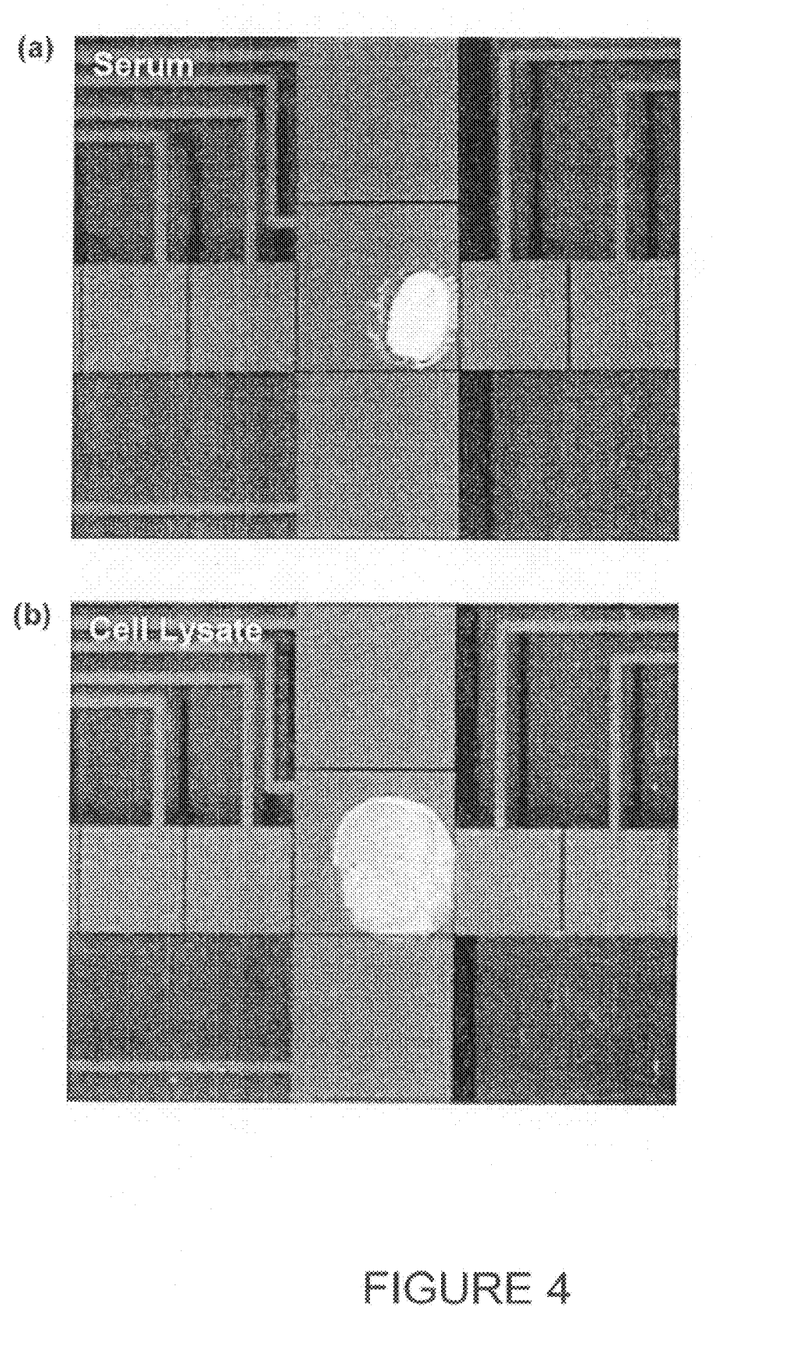
FIG. 4(a) shows an optical image of protein precipitates generated from droplets of (a) fetal bovine serum using the present DMF method.
FIG. 4(b) shows an optical image of protein precipitates generated from droplets of cell lysate (70 nL) using the present DMF method.

Protein precipitation is most useful as a sample cleanup step applied to complex mixtures—for example, precipitation is often used to purify proteins from plasma for proteome profiling.[32,33] To evaluate the potential for the new digital microfluidic method for such applications, we tested two model systems: fetal bovine serum (FBS) and cell lysate (CL). In both cases, the samples were found to be compatible with digital microfluidic manipulation and extraction. FIG. 4(a) shows an optical image of protein precipitates generated from droplets of (a) fetal bovine serum (FBS) and FIG. 4(b) shows an optical image of protein precipitates generated from droplets of cell lysate (70 nL) using the present DMF method.

FBS and CL solutions were more challenging to work with than protein standard solutions. First, dispensing droplets of cell lysate was difficult because the solution was so viscous. To solve this problem, the spacing between the top plate and the patterned bottom plate was decreased from 140 to 70 µm—this strategy (reducing the spacing between plates) has been shown to enhance dispensing of viscous solutions in DMF.[34] Second, precipitates formed from FBS and CL were particularly sticky, and in rare cases, the supernatant droplet could not be driven away from the extraction electrode. In such cases, we found that if a supplemental droplet of rinse solution was dispensed and driven to the extraction electrode, the combined droplet (rinse solvent+supernatant) could be successfully driven to waste. Upon application of these strategies (reduced inter-plate spacing and supplemental rinse droplets), the extraction process for FBS and CL became reliable and reproducible.

Protein recovery efficiencies from FBS and CL were determined using the fluorescent assay described above. In each case, performance was excellent (mean±S.D.)—84.0% (±7.8%) for FBS and 82.4% (±11.5%) for CL. These values are comparable to those reported for macro-scale techniques.[2] We note that higher protein recovery can be achieved by means of less rigorous rinsing; however, multiple rinse steps are typically used to ensure high purity of the processed sample. In summary, the performance of the new DMF-driven method is comparable to conventional techniques even for complex mixtures, which bodes well for our plans to integrate this procedure with other processing steps (such as enzymatic digestion[25]) for automated, miniaturized proteomic analysis.

In summary, the present invention provides a method for extracting proteins from heterogeneous fluids by precipitation using microfluidics. The method uses an automated protocol for precipitation of proteins onto surfaces, rinsing the precipitates to remove impurities, and resolubilization in buffer for further analysis. The method is compatible with proteins representing a range of different physicochemical properties, as well as with complex mixtures such as fetal bovine serum and cell lysate. In all cases, the quantitative performance (measured using a fluorescent assay for % recovery) was comparable to that of conventional techniques, which are manual and require more time. Thus, the method disclosed herein very advantageously facilitates the development of fully automated microfluidic methods for proteomic analyses.

A major advantage of the present process of isolating proteins is that when extracting proteins using the present digital microfluidic (DMF) method, one does not need to use centrifugation in the procedure. This is due to the very hydrophobic nature of the working surface (Teflon) on the electrode array and substrate and as a result attracting the protein precipitates and also because the length scales involved are very small, such that precipitation is fast. Centrifugation is a crucial step when extracting proteins using the conventional method (microcentrifuge tubes) in order to settle the precipitate (as a pellet) to the bottom of the tube. This is not needed in the present method which is a significant improvement, saving time and money.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES (1) Jiang, L.; He, L.; Fountoulakis, M., Comparison of protein precipitation methods for sample preparation prior to proteomic analysis, *Journal of Chromatography A* 2004, 1023, 317-320.

(2) Zellner, M.; Winkler, W.; Hayden, H.; Diestinger, M.; Eliasen, M.; Gesslbauer, B.; Miller, I.; Chang, M.; Kungl, A.; Roth, E.; Oehler, R., Quantitative validation of different protein precipitation methods in proteome analysis of blood platelets, *Electrophoresis* 2005, 26, 2481-2489.

(3) Park, J. W.; Lee, S. G.; Song, J. Y.; Joo, J. S.; Chung, M. J.; Kim, S. C.; Youn, H. S.; Kang, H. L.; Baik, S. C.; Lee, W. K.; Cho, M. J.; Rhee, K. H., Proteomic analysis of *Helicobacter pylori* cellular proteins fractionated by ammonium sulfate precipitation, *Electrophoresis* 2008, 29, 2891-2903.

(4) Sandhu, C.; Connor, M.; Kislinger, T.; Slingerland, J.; Emili, A., Global protein shotgun expression profiling of proliferating MCF-7 breast cancer cells, *Journal of Proteome Research* 2005, 4, 674-689.

(5) Englard, S.; Seifter, S., Precipitation Techniques, *Methods in Enzymology* 1990, 182, 285-300.

(6) Nandakumar, M. P.; Shen, J.; Raman, B.; Marten, M. R., Solubilization of trichloroacetic acid (TCA) precipitated microbial proteins via NaOH for two-dimensional electrophoresis, *Journal of Proteome Research* 2003, 2, 89-93.

(7) Simpson, R. J. *Purifying Proteins for Proteomics: A Laboratory Manual*, 1 ed.; Cold Spring Harbor Laboratory Press, 2004.

(8) Hirano, M.; Rakwal, R.; Shibato, J.; Agrawal, G. K.; Jwa, N. S.; Iwahashi, H.; Masuo, Y., New protein extraction/solubilization protocol for gel-based proteomics of rat (female) whole brain and brain regions, *Molecules and Cells* 2006, 22, 119-125.

(9) Freire, S. L. S.; Wheeler, A. R., Proteome-on-a-chip: Mirage, or on the horizon?, *Lab on a Chip* 2006, 6, 1415-1423.

(10) Tan, H. Y.; Loke, W. K.; Tan, Y. T.; Nguyen, N. T., A lab-on-a-chip for detection of nerve agent sarin in blood, *Lab on a Chip* 2008, 8, 885-891.

(11) Pollack, M. G.; Fair, R. B.; Shenderov, A. D., Electrowetting-based actuation of liquid droplets for microfluidic applications, *Applied Physics Letters* 2000, 77, 1725-1726.

(12) Lee, J.; Moon, H.; Fowler, J.; Schoellhammer, T.; Kim, C. J., Electrowetting and electrowetting-on-dielectric for microscale liquid handling, *Sensors and Actuators A-Physical* 2002, 95, 259-268.

(13) Barbulovic-Nad, I.; Yang, H.; Park, P. S.; Wheeler, A. R., Digital microfluidics for cell-based assays, *Lab on a Chip* 2008, 8, 519-526.

(14) Miller, E. M.; Wheeler, A. R., A digital microfluidic approach to homogeneous enzyme assays, *Analytical Chemistry* 2008, 80, 1614-1619.

(15) Srinivasan, V.; Pamula, V. K.; Fair, R. B., An integrated digital microfluidic lab-on-a-chip for clinical diagnostics on human physiological fluids, *Lab on a Chip* 2004, 4, 310-315.

(16) Srinivasan, V.; Pamula, V. K.; Fair, R. B., Droplet-based microfluidic lab-on-a-chip for glucose detection, *Analytica Chimica Acta* 2004, 507, 145-150.

(17) Moon, H.; Wheeler, A. R.; Garrell, R. L.; Loo, J. A.; Kim, C. J., An integrated digital microfluidic chip for multiplexed proteomic sample preparation and analysis by MALDI-MS, *Lab on a Chip* 2006, 6, 1213-1219.

(18) Wheeler, A. R.; Moon, H.; Bird, C. A.; Loo, R. R. O.; Kim, C. J.; Loo, J. A.; Garrell, R. L., Digital microfluidics with in-line sample purification for proteomics analyses with MALDI-MS, *Analytical Chemistry* 2005, 77, 534-540.

(19) Wheeler, A. R.; Moon, H.; Kim, C. J.; Loo, J. A.; Garrell, R. L., Electrowetting-based microfluidics for analysis of peptides and proteins by matrix-assisted laser desorption/ionization mass spectrometry, *Analytical Chemistry* 2004, 76, 4833-4838.

(20) Chang, Y. H.; Lee, G. B.; Huang, F. C.; Chen, Y. Y.; Lin, J. L., Integrated polymerase chain reaction chips utilizing digital microfluidics, *Biomedical Microdevices* 2006, 8, 215-225.

(21) Fouillet, Y.; Jary, D.; Chabrol, C.; Claustre, P.; Peponnet, C., Digital microfluidic design and optimization of classic and new fluidic functions for lab on a chip systems, *Microfluidics and Nanofluidics* 2008, 4, 159-165.

(22) Abdelgawad, M.; Freire, S. L. S.; Yang, H.; Wheeler, A. R., All-terrain droplet actuation, *Lab on a Chip* 2008, 8, 672-677.

(23) Zhao, Y. J.; Cho, S. K., Micro air bubble manipulation by electrowetting on dielectric (EWOD): transporting, splitting, merging and eliminating of bubbles, *Lab on a Chip* 2007, 7, 273-280.

(24) Brassard, D.; Malic, L.; Normandin, F.; Tabrizian, M.; Veres, T., Water-oil core-shell droplets for electrowetting-based digital microfluidic devices, *Lab on a Chip* 2008, 8, 1342-1349.

(25) Luk, V. N.; Mo, G. C. H.; Wheeler, A. R., Pluronic additives: A solution to sticky problems in digital microfluidics, *Langmuir* 2008, 24, 6382-6389.

(26) Chatterjee, D.; Hetayothin, B.; Wheeler, A. R.; King, D. J.; Garrell, R. L., Droplet-based microfluidics with non-aqueous solvents and solutions, *Lab on a Chip* 2006, 6, 199-206.

(27) Bradford, M. M., Rapid and Sensitive Method for Quantitation of Microgram Quantities of Protein Utilizing Principle of Protein-Dye Binding, *Analytical Biochemistry* 1976, 72, 248-254.

(28) Bohlen, P.; Stein, S.; Dairman, W.; Udenfrie. S, Fluorometric Assay of Proteins in Nanogram Range, *Archives of Biochemistry and Biophysics* 1973, 155, 213-220.

(29) Udenfrie, S.; Stein, S.; Bohlen, P.; Dairman, W., Fluorescamine—Reagent for Assay of Amino-Acids, Peptides, Proteins, and Primary Amines in Picomole Range, *Science* 1972, 178, 871-872.

(30) Noble, J. E.; Knight, A. E.; Reason, A. J.; Di Matola, A.; Bailey, M. J. A., A comparison of protein quantitation assays for biopharmaceutical applications, *Molecular Biotechnology* 2007, 37, 99-111.

(31) Bergo, H. O.; Christiansen, C., Determination of low levels of protein impurities in phospholipid samples, *Analytical Biochemistry* 2001, 288, 225-227.

(32) He, P.; He, H. Z.; Dai, J.; Wang, Y.; Sheng, Q. H.; Zhou, L. P.; Zhang, Z. S.; Sun, Y. L.; Liu, F.; Wang, K.; Zhang, J. S.; Wang, H. X.; Song, Z. M.; Zhang, H. R.; Zeng, R.; Zhao, X. H., The human plasma proteome: Analysis of Chinese serum using shotgun strategy, *Proteomics* 2005, 5, 3442-3453.

(33) Adkins, J. N.; Varnum, S. M.; Auberry, K. J.; Moore, R. J.; Angell, N. H.; Smith, R. D.; Springer, D. L.; Pounds, J. G., Toward a human blood serum proteome—Analysis by multidimensional separation coupled with mass spectrometry, *Molecular & Cellular Proteomics* 2002, 1, 947-955.

(34) Cho, S. K.; Moon, H. J.; Kim, C. J., Creating, transporting, cutting, and merging liquid droplets by electrowetting-based actuation for digital microfluidic circuits, *Journal of Microelectromechanical Systems* 2003, 12, 70-80.

Therefore what is claimed is:

1. A digital microfluidic based method for protein extraction by precipitation from heterogeneous mixtures, comprising the steps of:

a) providing a digital microfluidic device having an array of actuating electrodes formed on a substrate surface, a coating having a hydrophobic working surface coating the substrate surface and array of actuating electrodes, an actuating electrode controller for exciting or de-exciting said actuating electrodes for translating liquid droplets over said hydrophobic working surface;

b) dispensing one or more first sample droplets containing protein, onto one or more first positions on the hydrophobic working surface, and dispensing one or more second droplets containing a protein precipitant onto one or more second positions on the hydrophobic working surface;

c) translating one or more first sample droplets with one or more second droplets to one or more corresponding designated protein extraction positions on the hydrophobic working surface such that said first and said second droplets mix to form one or more secondary droplets;

d) incubating one or more secondary droplets at said one or more designated extraction positions to precipitate said protein contained in the one or more said first droplets onto the one or more said designated protein extraction positions to separate the precipitated protein from a supernatant above the precipitated protein;

e) actuating one or more of said discrete electrodes associated with the one or more corresponding extraction positions to remove the one or more droplets containing the supernatant from the one or more corresponding extraction positions to leave behind the precipitated protein;

f) dispensing one or more third droplets containing wash solution onto said hydrophobic working surface and translating said one or more third droplets to said one or more corresponding extraction positions to wash the precipitated protein;

g) drying the precipitated protein at the one or more extraction positions;

h) dispensing one or more fourth droplets containing resolubilization solution onto said hydrophobic working surface and translating said one or more fourth droplets to said one or more corresponding extraction positions to produce one or more droplets of resolubilized protein; and i) translating the one or more droplets of resolubilized protein to one or more collection points on said hydrophobic working surface and collecting the one or more droplets of resolubilized protein.

2. The method according to claim 1 wherein said one or more sample droplets include protein standards, bovine serum albumin, myoglobin, insulin, fibrinogen, fibronectin, fetal bovine serum, cell lysate, tissue powder, plasma, whole blood, or mixtures thereof.

3. The method according to claim 1 wherein said protein precipitant is selected from the group consisting of trichloroacetic acid (TCA), acetonitrile, acetone, ethanol, mercaptoethanol, chloroform, and polyethylene glycol, dextran, ammonium sulfate, and mixtures thereof.

4. The method according to claim 1 wherein said resolubilization solution is selected from the group consisting of borate, sodium hydroxide, potassium carbonate, tris(hydroxymethyl) aminomethane hydrochloride (Tris-HCl), urea, thiourea, trizma base, triton X-100, 3-[(cholamidopropyl) dimethylamino]-1-propanesulfonate (CHAPS), dithiothreitol (DTT), and sodium dodecyl sulfate (SDS), LKP ampholines, and mixtures thereof.

5. The method according to claim 1 including a step of analyzing said supernatant, said precipitated protein, or both.

6. The method according to claim 5 wherein the step of analyzing said supernatant, said precipitated protein, or both, performed by detecting signals emitted from the secondary droplets using a device capable of detecting a signal from the secondary droplets selected from the group consisting of optical sensors, optical detectors comprising a light source and a photodetector, optical detectors that measure properties selected from the group consisting of absorbance, fluorescence, epifluorescence, chemiluminescence and mixtures thereof, UV light detectors, radiometric detectors, scanning, imaging, and confocal microscopy detectors, CCD cameras, and microplate readers.

7. The method according to claim 1 wherein steps b), c), d) e), f), g), h) and i) are conducted under control of a computer controller interfaced to said digital microfluidic device.

8. The method according to claim 1 wherein steps b), c), d) e), f), g), h), i) and j) are conducted under control of a computer controller interfaced to said digital microfluidic device.

9. A digital microfluidic based method for protein extraction by precipitation from heterogeneous mixtures, comprising the steps of:
  a) providing a digital microfluidic device having an array of actuating electrodes formed on a substrate surface, a coating having a hydrophobic working surface coating the substrate surface and array of actuating electrodes, an actuating electrode controller for exciting or de-exciting said actuating electrodes for translating liquid droplets over said hydrophobic working surface;
  b) depositing a protein precipitant on one or more designated protein extraction positions on the working surface;
  c) dispensing one or more first sample droplets containing protein onto one or more first positions on the hydrophobic working surface;
  d) translating each of the one or more first droplets to one or more of the corresponding designated protein extraction positions on the working surface such that said one or more first droplets mix with said protein precipitant in said one or more designated protein extraction positions to form one or more secondary droplets;
  e) incubating said one or more secondary droplets at said one or more designated extraction positions to precipitate said protein contained in the one or more said first droplets onto the one or more said designated protein extraction positions to separate the precipitated protein from a supernatant above the precipitated protein;
  f) actuating one or more of said discrete electrodes associated with the one or more corresponding extraction positions to remove the one or more droplets of containing the supernatant from the one or more corresponding extraction positions to leave behind the precipitated protein;
  g) dispensing one or more third droplets containing wash solution onto said working surface and translating said one or more third droplets to said one or more corresponding extraction positions to wash the precipitated protein;
  h) drying the precipitated protein at the one or more extraction positions;
  i) dispensing one or more fourth droplets containing resolubilization solution onto said hydrophobic working surface and translating said one or more fourth droplets to said one or more corresponding extraction positions to produce one or more droplets of resolubilized protein; and
  j) translating the one or more droplets of resolubilized protein to one or more collection points on said hydrophobic working surface and collecting the one or more droplets of resolubilized protein.

10. The method according to claim 9 wherein said protein precipitant is in liquid form.

11. The method according to claim 9 wherein said protein precipitant is in solid form which is coated onto the one or more corresponding extraction positions.

12. The method according to claim 11 wherein said protein precipitant in solid form is ammonium sulfate and trichloroacetic acid.

13. The method according to claim 9 whereinsaid one or more sample droplets include protein standards, bovine serum albumin, myoglobin, insulin, fibrinogen, fibronectin, fetal bovine serum, cell lysate, tissue powder, plasma, whole blood, or mixtures thereof.

14. The method according to claim 9 wherein said protein precipitant is selected from the group consisting of trichloroacetic acid (TCA), acetonitrile, acetone, ethanol, mercaptoethanol, chloroform, and polyethylene glycol, dextran, ammonium sulfate, and mixtures thereof.

15. The method according to claim 9 wherein said resolubilization solution is selected from the group consisting of borate, sodium hydroxide, potassium carbonate, tris(hydroxymethyl) aminomethane hydrochloride (Tris-HCl), urea, thiourea, trizma base, triton X-100, 3-[(cholamidopropyl) dimethylamino]-1-propanesulfonate (CHAPS), dithiothreitol (DTT), and sodium dodecyl sulfate (SDS), LKP ampholines, and mixtures thereof.

16. The method according to claim 9 including a step of analyzing said supernatant, said precipitated protein, or both.

17. The method according to claim 16 wherein the step of analyzing said supernatant, said precipitated protein, or both, performed by detecting signals emitted from the secondary droplets using a device capable of detecting a signal from the secondary droplets selected from the group consisting of optical sensors, optical detectors comprising a light source and a photodetector, optical detectors that measure properties selected from the group consisting of absorbance, fluorescence, epifluorescence, chemiluminescence, and mixtures thereof, UV light detectors, radiometric detectors, scanning, imaging, and confocal microscopy detectors, CCD cameras, and microplate readers.

* * * * *